(12) United States Patent
Van De Laar et al.

(10) Patent No.: US 11,944,464 B2
(45) Date of Patent: Apr. 2, 2024

(54) METHODS AND SYSTEM FOR DETECTING INHALATIONS AND EXTRACTING MEASURES OF NEURAL RESPIRATORY DRIVE FROM AN EMG SIGNAL

(71) Applicant: KONINKLIJKE PHILIPS N.V., Eindhoven (NL)

(72) Inventors: Jakob Van De Laar, Oosterhout (NL); Sandrine Magali Laure Devot, Cologne (DE); Rene Martinus Maria Derkx, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 187 days.

(21) Appl. No.: 16/605,545

(22) PCT Filed: Apr. 13, 2018

(86) PCT No.: PCT/EP2018/059499
§ 371 (c)(1),
(2) Date: Oct. 16, 2019

(87) PCT Pub. No.: WO2018/192843
PCT Pub. Date: Oct. 25, 2018

(65) Prior Publication Data
US 2020/0121260 A1    Apr. 23, 2020

(30) Foreign Application Priority Data
Apr. 20, 2017   (EP) ...................................... 17167319

(51) Int. Cl.
*A61B 5/00*       (2006.01)
*A61B 5/08*       (2006.01)
(Continued)

(52) U.S. Cl.
CPC .............. *A61B 5/7278* (2013.01); *A61B 5/08* (2013.01); *A61B 5/316* (2021.01); *A61B 5/389* (2021.01); *A61B 5/4041* (2013.01)

(58) Field of Classification Search
CPC ......... A61B 5/08; A61B 5/389; A61B 5/4041; A61B 5/7278
See application file for complete search history.

(56) References Cited

U.S. PATENT DOCUMENTS

| 4,248,240 A | 2/1981 | Groningen |
| 6,411,843 B1 * | 6/2002 | Zarychta ............. A61M 16/024 128/204.23 |

(Continued)

FOREIGN PATENT DOCUMENTS

| JP | 2016083369 A | 5/2016 |
| WO | 2013045920 A1 | 4/2013 |
| WO | 2015044010 A1 | 4/2015 |

OTHER PUBLICATIONS

Reilly, C. et al., "Neural respiratory drive measured during inspiratory threshold loading and acute hypercapnia in healthy individuals: Neural respiratory drive measurement", Experimental Physiology, vol. 98, No. 7, Apr. 2013.

(Continued)

*Primary Examiner* — Charles A Marmor, II
*Assistant Examiner* — Raymond P Dulman

(57) ABSTRACT

The invention provides a method (10) for detecting a neural respiratory drive measure of a user. The method includes obtaining (100) an EMG signal and processing (200, 280) the EMG signal to produce a surrogate respiration signal and a processed EMG signal. Inhalations of the user are then detected (300) based on the surrogate respiration signal. The detected inhalations are then used in conjunction with the (Continued)

processed EMG signal to determine (400) a neural respiratory drive measure of the user.

15 Claims, 3 Drawing Sheets

(51) Int. Cl.
*A61B 5/316* (2021.01)
*A61B 5/389* (2021.01)

(56) References Cited

U.S. PATENT DOCUMENTS

| | | | |
|---|---|---|---|
| 6,588,423 B1* | 7/2003 | Sinderby | A61M 16/026 128/204.23 |
| 2003/0166996 A1* | 9/2003 | Kim | A61B 5/165 600/300 |
| 2004/0044377 A1* | 3/2004 | Larsson | A61B 5/389 607/42 |
| 2006/0060190 A1 | 3/2006 | Sinderby | |
| 2011/0060215 A1* | 3/2011 | Tupin, Jr. | A61B 5/091 600/425 |
| 2013/0310699 A1 | 11/2013 | Hart et al. | |
| 2014/0142395 A1* | 5/2014 | Sattler | A61B 5/725 128/204.23 |
| 2014/0296728 A1* | 10/2014 | Sinderby | A61B 5/24 600/529 |
| 2016/0199606 A1 | 7/2016 | Eger | |
| 2018/0344194 A1* | 12/2018 | Eger | A61B 5/4836 |
| 2018/0360376 A1* | 12/2018 | Garcia Molina | A61B 5/4809 |
| 2019/0073525 A1* | 3/2019 | Kim | G06F 3/017 |
| 2019/0231268 A1* | 8/2019 | Denk | A61B 5/389 |

OTHER PUBLICATIONS

Hodges, P. et al., "Postural activity of the diaphragm is reduced in humans when respiratory demand increases", Journal of Physiology, Sep. 2001.

International Search Report and Written Opinion, International Application No. PCT/EP2018/059499, dated Apr. 13, 2018.

P.B. Murphy, et. al., "Chronic obstructive pulmonary disease, Neural respiratory drive as a physiological biomarker to monitor change during acute exacerbations of COPD", Thorax 2010, May 19, 2011.

E. Hanafin Breslin, et. al., "Respiratory muscle function in patients with chronic obstructive pulmonary disease", Heart & Lung, vol. 24, No. 4, Jul./Aug. 1996, pp. 271-285.

M.L. Duiverman, et.al., "Reproducibility and responsiveness of a non-invsaive EMG technique of the respiratory muscles in COPD patients and in healthy subjects", J. Appl. .Physiol., Dec. 5, 2003.

A. De Troyer, et. al., "Respiratory Action of the Intercostal Muscles", Physiol Rev, vol. 85, pp. 717-756, 2005.

J.N. Han, et. al., "Respiratory function of the rib cage muscles," Eur Respir J, vol. 6, pp. 722-728, 1993.

A. Bartolo, et. al., "Analysis of diaphragm EMG signals: comparison of gating vs. subtraction for removal of ECG contamination", Journal of applied physiology, 80(6), pp. 1898-1902, Jun. 1996.

J. Pan and W. J. Tompkins. A real-time QRS detection algorithm, IEEE Trans. Biomed. Eng., vol. 32, No. 3, pp. 230-236, 1985.

Van Eykern et al. Two similar averages for respiratory muscle activity, Letter to editor, J. Appl. Physiology 90:2014-2015, 2001.

D.T. Mewett, et.al., "Reducing power line interference in digitized electromyogram recordings by spectrum Interpolation", Med. Biol. Eng. Comput., 2004, 42, 524-531.

P.S. Hamilton, "A Comparison of Adaptive and Nonadaptive Filters for Reduction of Power Line Interference in the ECG", IEEE Transaction on Biomedial Engineering, vol. 43, No. 1, Jan. 1999.

Estrada, L. et al., "EMG-Derived Respiration Signal using the Fixed Sample Entropy during an Inspiratory Load Protocol", IEEE, 2015.

Reilly, C. et al., "Neural respiratory drive measured during inspiratory threshold loading and acute hypercapnia in healthy individuals", Exp Physiol 98.7 (2013) pp. 1190-1198.

Suh, E. et al., "Neural respiratory drive predicts clinical deterioration and safe discharge in exacerbations of COPD", Chronic obstructive pulmonary disease, Thorax 2015;70:1123-1130.

* cited by examiner ial Application Serial No. PCT/EP2018/059499 is hereby incorporated by reference herein.

METHODS AND SYSTEM FOR DETECTING INHALATIONS AND EXTRACTING MEASURES OF NEURAL RESPIRATORY DRIVE FROM AN EMG SIGNAL

CROSS-REFERENCE TO PRIOR APPLICATIONS

This application is the U.S. National Phase application under 35 U.S.C. § 371 of International Application Serial No. PCT/EP2018/059499, filed on 13 Apr. 2018, which claims the benefit of European Application Serial No. 17167319.7, filed on 20 Apr. 2017. International Application Serial No. PCT/EP2018/059499 is hereby incorporated by reference herein.

FIELD OF THE INVENTION

This invention relates to the field of signal processing, and more specifically to the field of electromyogram (EMG) signal processing.

BACKGROUND OF THE INVENTION

In patients with chronic obstructive pulmonary disease (COPD) and other respiratory diseases, the assessment of parasternal and/or diaphragm muscle activity measured from surface EMGs can be used to estimate the intensity, timing and duration of patient respiratory effort. This can serve as an indicator of the balance between respiratory muscle load and respiratory muscle capacity. The EMG signals during inhalation are related to the neural respiratory drive (NRD). During lung hyperinflation, as observed in COPD patients during acute exacerbation, there is a change in the balance between respiratory muscle load and capacity, which is reflected in the neural respiratory drive. A lower capacity and higher load result in an increased NRD. The EMG signals measured from respiratory muscles, for example from parasternal muscles at the $2^{nd}$ intercostal space or from the diaphragm at the abdomen, via EMG electrodes, during inhalation can be used as an indicator of the deterioration or improvement of the patient. This may also be used as a predictor of hospital readmission after discharge.

In order to assess the respiratory muscle activity during an inhalation, the time intervals corresponding to inhalations need to be identified. Usually, signals measured with a nasal cannula are used to determine the inhalation intervals. For example, a nasal cannula may be connected to a differential pressure transducer to identify inspiration and expiration phases (as air flows in and out respectively), thus to guide the NRD manual analysis. However, in practice, the signals from nasal cannulas are often unreliable and/or contaminated with signal artifacts. This is particularly frequent in patients with COPD admitted to hospital with an acute exacerbation, who often experience difficulties in breathing through the nose and/or erratic breathing. The low quality of the nasal cannula signals often results in the algorithm being unable to compute an NRD value because inhalation phases cannot be detected reliably from the nasal cannula signal. In addition, if NRD values are being computed, they may be incorrect because of incorrect inhalation phase detection from the nasal cannula signal, potentially leading to a misinterpretation of the patient's condition. In addition, wearing a nasal cannula can be uncomfortable for the patient, especially during long-term continuous recordings.

There are several causes of poor signal quality from the nasal cannula. Firstly, the nasal cannula may not be properly inserted into the nostrils, or it may become loose during the course of a measurement period. In addition, signal artifacts may be caused by movements of the cannula inside the nostrils, which may occur when the patient is moving or coughing. Another common problem is that the patient may breathe partly, or completely, through the mouth, in which case the nasal cannula signal may be very weak and noisy. Finally, large baseline offsets, which may lead to false inhalation identification, may be present in the nasal cannula signal.

There is therefore a need for a more reliable way to determine the inhalation phases within an EMG signal, and without requiring significant additional hardware.

SUMMARY OF THE INVENTION

The invention is defined by the claims.

According to examples in accordance with an aspect of the invention, there is provided a method for extracting a neural respiratory drive measure of a user, the method comprising:
  obtaining an EMG signal;
  processing the EMG signal to produce a processed EMG signal;
  processing the EMG signal to produce a surrogate respiration signal;
  detecting inhalations of the user based on the surrogate respiration signal; and
  determining a neural respiratory drive measure based on the detected inhalations and the processed EMG signal.

This method derives the inhalations of a user solely from an EMG signal of the user. Inhalation detection is typically performed by way of a nasal cannula; however, this can be inaccurate and uncomfortable for the user. By detecting the inhalations of the user using a surrogate respiration signal derived solely from an EMG signal, a more accurate measurement may be obtained. This is due to the fact that the EMG signal measures muscle activity rather than airflow, meaning that the user may breathe through either the nose or mouth without disrupting the EMG signal. In addition, as an EMG signal is measured by way of external electrodes, the measurement is more comfortable for the user.

The EMG signal is also processed to produce a processed EMG signal, such as an RMS of the EMG signal or a mean absolute value of the EMG signal. By detecting the inhalations of the user from the surrogate respiration signal and time aligning the inhalations with the processed EMG signal, it is possible to identify a neural respiratory drive measure of the user. Time aligning refers to the process of aligning two signals so that they show the same time window. The neural respiratory drive measure of the user, for example the peak-inspiratory RMS EMG values, may form the basis of many clinical parameters, such as the NRD, of the user.

A raw EMG signal obtained directly from a user often contains a large amount of noise and ECG signals. By processing the EMG signal to produce a surrogate respiration signal, the signal to noise ratio may be increased, leading to a greater accuracy of inhalation detection. Inhalations may be detected from the surrogate respiration signal by way of a simple threshold. In other words, if the signal rises above a predetermined value, an inhalation is detected. Alternatively, a signal dependent threshold may be used.

In an embodiment, processing the EMG signal to produce a surrogate respiration signal comprises performing spike removal on the EMG signal.

Transient spikes may appear in the EMG signal for a number of reasons, such as a pacemaker of the user. These spike signals may be non-physiological, meaning that they do not represent muscle activity, and so do not contribute useful information to the EMG signal. The transient spikes may be also be physiological, for example due to the ECG signals. By removing the spikes from the EMG signal, the signal to noise ratio is increased.

In some embodiments, processing the EMG signal to produce a surrogate respiration signal comprises applying a first high pass filter to the EMG signal.

In further embodiments, the first high pass filter has a cutoff frequency of greater than or equal to 150 Hz. Typically, 200 Hz is chosen as the cutoff frequency.

The EMG signal will typically contain ECG signal contamination. By applying a first high pass filter to the EMG signal, it is possible to reduce and/or remove the ECG signal contamination. In addition, applying the first high pass filter may also reduce various low-frequency artifacts and noise in the EMG signal.

In an arrangement, the processing of the EMG signal to produce a surrogate respiration signal comprises performing envelope detection on the EMG signal, wherein the envelope detection comprises:
  applying a rectification operator to the EMG signal, to generate a second EMG signal; and
  applying a low pass filter to the second EMG signal.

The envelope detection computes a low-frequency envelope measure of the high-frequency EMG signal, which is representative of the breathing of the user. By applying a rectification operator to the EMG signal, it is possible to prevent the signal averaging to zero. The low pass filter is then applied to the second EMG signal, thereby producing an EMG envelope signal, which may then be used as the basis of the inhalation detection. The low pass filter additionally acts as the final smoothing stage for the signal to reduce the noise in the EMG signal.

In a further arrangement, the second EMG signal comprises an energy-like measure of the EMG signal.

In a yet further arrangement, the energy-like measure of the EMG signal comprises at least one of the Teager-Kaiser energy and the conventional energy.

The Teager-Kaiser energy operator is efficient and simple to implement, meaning that it is possible to compute an energy-like measure of the EMG signal without negatively impacting the performance of the system. The conventional energy is simply the sum of a number of squared signal values.

In an embodiment, the rectification operator comprises at least one of the absolute operator and the square operator.

By applying a rectifying operator to the EMG signal, such as the absolute or square operator, it is possible rectify the EMG signal and perform signal envelope detection by way of the low pass filter.

In some designs, processing the EMG signal to produce a surrogate respiration signal comprises downsampling the EMG signal.

Downsampling is the process of reducing the sampling rate of a signal, which is used to reduce the size of the signal data set. In this way, it is possible to reduce the memory and processing requirements for processing the EMG signal.

In an embodiment, processing the EMG signal to produce a surrogate respiration signal comprises applying a median filter to the EMG signal.

By using a median filter, it is possible to remove any remaining residual spike signals, which were not removed by initial spike removal or the first high pass filter, from the EMG signal.

In an arrangement, processing the EMG signal to produce a surrogate respiration signal comprises applying a second high pass filter to the EMG signal.

By applying the second high pass filter to the EMG signal, the baseline component of the signal is removed. In this way, underlying signal trends, which are not relevant to the determination of inhalation phases from the EMG signal, may be removed. This may lead to a more accurate surrogate respiration signal, and so more accurate inhalation detection.

In some arrangements, the method further comprises computing the neural respiratory drive of the user based on the neural respiratory drive measure.

By computing the neural respiratory drive of the user, it is possible to monitor the respiratory function and health of the user.

According to examples in accordance with an aspect of the invention, there is provided a computer program comprising computer program code means which is adapted, when said computer is run on a computer, to implement the method described above.

According to examples in accordance with an aspect of the invention, there is provided an inhalation detection system comprising:
  an EMG electrode adapted to measure the EMG signal; and
  a controller, wherein the controller is adapted to:
    obtain an EMG signal;
    process the EMG signal to produce a processed EMG signal;
    process the EMG signal to produce a surrogate respiration signal;
    detect inhalations of the user based on the surrogate respiration signal; and
    determine a neural respiratory drive measure based on the detected inhalations and the processed EMG signal.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for detecting a neural respiratory drive measure of a user. The method includes obtaining an EMG signal and processing the EMG signal to produce a surrogate respiration signal and a processed EMG signal. Inhalations of the user are then detected based on the surrogate respiration signal. The detected inhalations are then used in conjunction with the processed EMG signal to determine a neural respiratory drive measure of the user.

Figure 1:
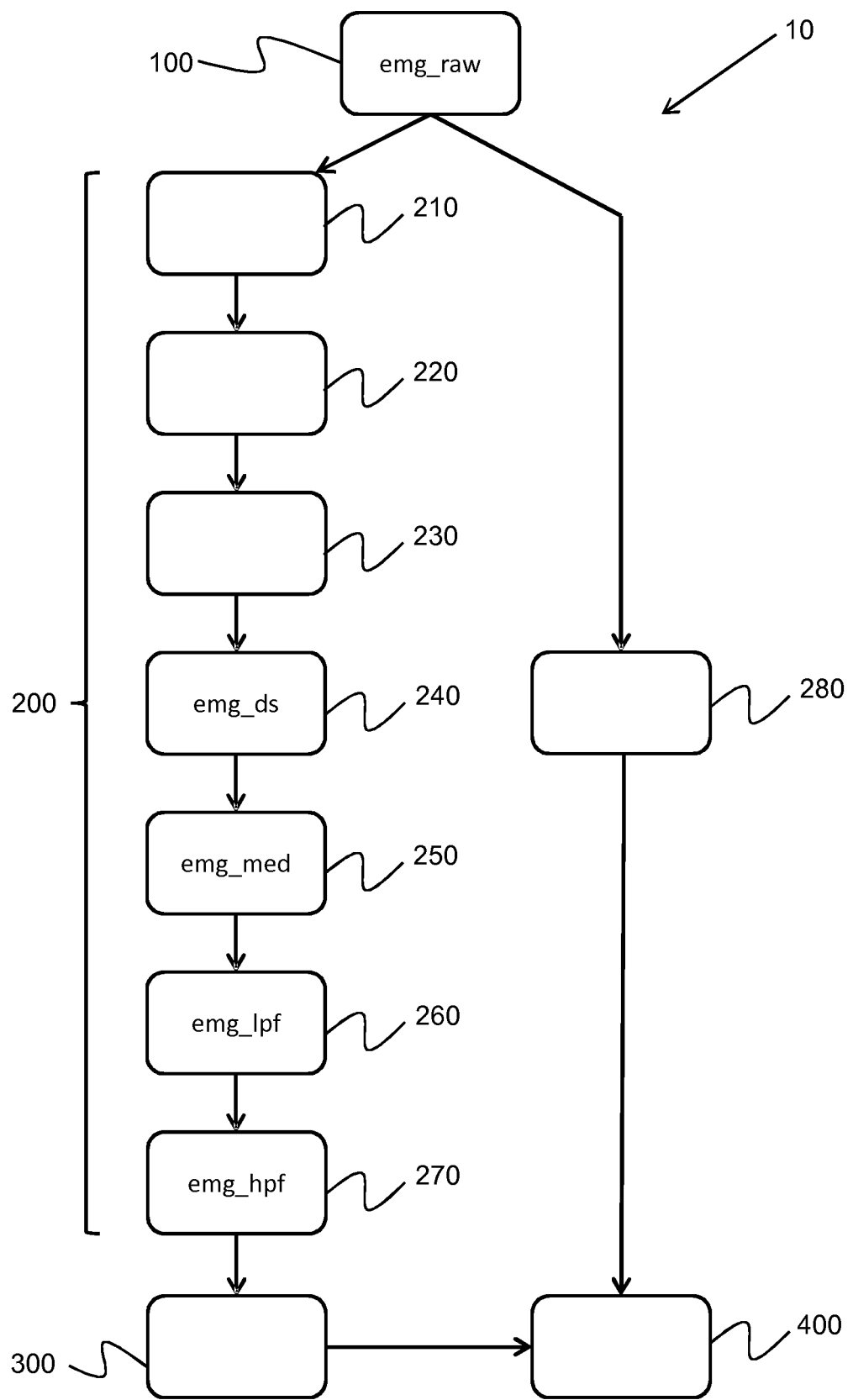
FIG. 1 shows a method according to an embodiment of the invention.

FIG. 1 shows a method 10 for detecting inhalations of a user and using these to determine a neural respiratory drive measure of the user, according to an embodiment.

In step 100 an EMG signal is obtained from the user. For example, the EMG signal may be measured by way of two EMG electrodes placed on the second intercostal space of the patient, with one electrode located either side of the sternum. An exemplary EMG signal measured in this way is shown in the graphs 500 of FIG. 2 by the emg_raw plot 510.

As the obtained EMG signal will contain a large amount of noise and ECG contamination, the EMG signal may undergo a series of processing steps 200 in order to produce a surrogate respiration signal to be used in inhalation detection.

In step 210, spike removal may be performed on the EMG signal. Transient, non-physiological spikes may appear in the EMG signal, for example due to a pacemaker of the user. The transient spikes may be also be physiological, for example due to the ECG signals. By removing the spikes from the EMG signal, the signal to noise ratio is increased.

In step 220, a first high pass filter may be applied to the EMG signal. The first high pass filter has a cutoff frequency of greater than or equal to 150 Hz. Typically, 200 Hz is chosen as the cutoff frequency.

Applying the first high pass filter to the EMG signal will reduce the low-frequency noise and motion artifacts in the signal. The EMG signal may contain tonic activity signals, which correspond to slow physiological responses in the muscles, such as tonic intercostal muscle activity associated with a specific posture at the measurement location of the EMG signal. These signals are not useful for performing inhalation detection and so act as noise within the EMG signal. Due to the low frequency nature of the tonic activity signals, they may be suppressed and/or removed up to a certain extent by the first high pass filter.

In addition to tonic activity, the EMG signal may also contain substantial ECG signal contamination. ECG signals typically lie in the frequency range 0.01-300 Hz, whereas EMG signals lie in the range 50-3000 Hz. By applying a high pass filter with a cutoff frequency of 200 Hz to the obtained EMG signal, the ECG contamination may be reduced and/or eliminated. Movement artifacts and additional noise may arise from a number of sources, such as shifting of the EMG electrodes due to the motion of the user's chest or pulling on the cables connected to the electrodes. These may also be reduced and/or removed by way of the first high pass filter.

In step 230, a rectification operator is applied to the EMG signal, generating a second EMG signal. Rectification is the translation of the EMG signal to a single polarity. Full-wave rectification can be readily achieved by way of the absolute operator. Alternatively, rectification may also be achieved by way of the square operator, which squares the signal values. This is done to ensure that the signal does not average to zero when undergoing statistical analysis. In another example, the rectification of the EMG signal may be achieved by performing a Hilbert transform on the analytical EMG signal.

The rectification operator may produce an absolute value or energy-like measure of the EMG signal such as the conventional or Teager-Kaiser energy.

Forming the surrogate respiration signal from an absolute value or energy-like measure of the EMG signal greatly simplifies the process of performing inhalation detection. The conventional energy is defined as (a smoothed version of) the square of the signal. The Teager-Kaiser energy of the EMG signal is calculated using the Teager-Kaiser operator, as follows:

$$\Psi(X(t)) = \dot{x}^2(t) - x(t)\ddot{x}(t),$$

where: $\Psi$ is the Teager-Kaiser operator; x is a function of time, such as the EMG signal; $\dot{x}$ is the first derivative of function x with respect to time; and $\ddot{x}$ is the second derivative of function x with respect to time. As the absolute value, as well as conventional and Teager-Kaiser energy operators are not computationally complex, they may be implemented without significantly increasing the processing requirements of the system.

In step 240, downsampling may be performed on the EMG signal.

Downsampling reduces the sampling rate of the EMG signal, thereby reducing the size of the signal data set. This in turn may reduce processing power and memory required to analyze and manipulate the signal. The inhalation detection may be based on the low frequency nature of the EMG signal envelope, meaning that a reduction in the sampling rate of the signal does not lead to a reduction in the performance or accuracy of the inhalation detection. In other words, downsampling may be performed to increase the efficiency of the inhalation detection process, whilst maintaining the accuracy of the results. The plot emg_ds 520 shows the result of performing downsampling on the energy-like measure of the spike-removed (partially), high-pass filtered emg_raw signal 510.

In step 250, a median filter may be applied to the EMG signal.

Figure 2:
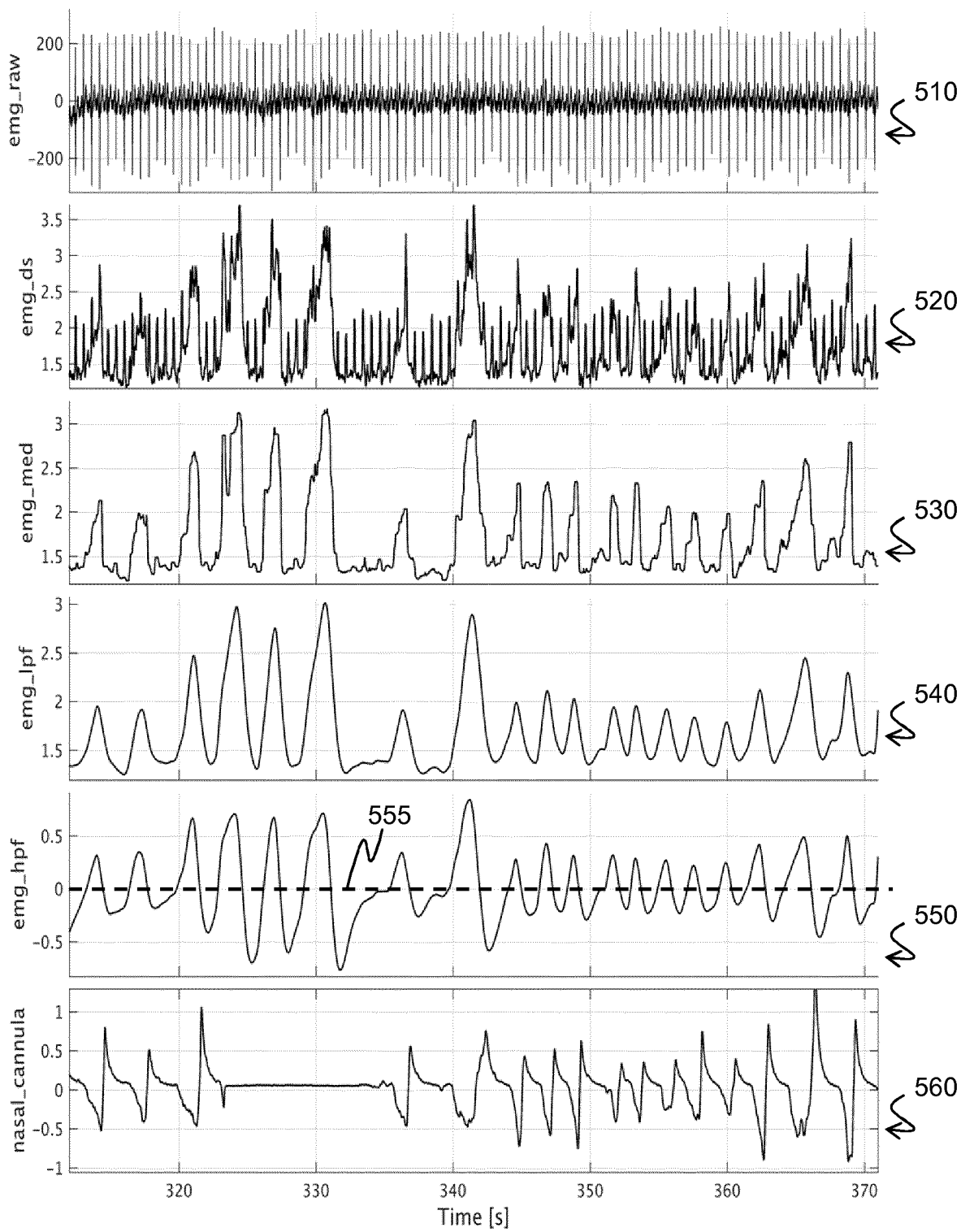
FIG. 2 shows a series of plots illustrating the EMG signal during various method steps of FIG. 1 in comparison to a signal taken from a nasal cannula.

The median filter is a non-linear filter to suppress any spikes that remain in the EMG signal, whilst not smearing out those spikes. The plot emg_med 530 of FIG. 2 shows the result of applying a median filter to the downsampled EMG signal energy, emg_ds 520. The reduction in the number of remaining spikes in the EMG signal energy due to the median filter can be clearly seen by comparing the two plots. The filter works by obtaining a value in a sequence of signal values, comparing it to neighboring values and taking the median value as the output value for that location within the sequence. The filter may be defined, for a sequence of signal values as follows:

$$y(n) = F\{x(n), L\},$$

where: y(n) is the $n^{th}$ output value; F is the median filter operator; x(n) is the $n^{th}$ signal value; and L is the number of consecutive signal values used to compute the output value. For example, for L=3, only the signals on either side of x(n), i.e. x(n+1) and x(n−1), are used in the comparison to compute the output value y(n). In another example, the last three values in the series may be used, i.e. x(n), x(n−1) and x(n−2). For each signal value, according to the first example, the output value, y(n), is given as the median value of the sequence:

$$x[n-L/2] \text{ to } x[n+L/2-1], \text{ for even } L, \text{ or}$$

$$x[n-(L-1)/2] \text{ to } x[n+(L-1)/2], \text{ for odd } L.$$

In step 260, a low pass filter is applied to the EMG signal.

A low pass filter is applied to the previously rectified and subsequently cleaned EMG signal to perform envelope estimation and the final stage of signal smoothing. The steps 230 to 260 inclusive perform the function of envelope detection. Alternatively, envelope detection may be performed by only steps 230 and 260. The plot emg_lpf 540 shows the final EMG envelope signal as a result of applying the low pass filter to the median filtered, downsampled, rectified EMG signal, emg_med 530. By comparing the two plots, it is clear to see that any high frequency components of the emg_med plot have been removed to provide the envelope signal shown in the emg_lpf plot.

In step 270, a second high pass filter may be applied to the EMG signal.

The second high pass filter may be introduced to remove the baseline, or background, component signals from the EMG signal. Baseline removal is used to obtain a signal that oscillates around zero, which may be required for the detection of inhalations. Additionally, baseline removal may reduce the effect of background signals, which may introduce false trends to the data, and emphasize the true signal. This increases the accuracy of the inhalation detection. The plot emg_lpf 550, the surrogate respiration signal, shows the result of applying the second high pass filter to the envelope signal, emg_lpf 540.

The steps described above form a processing branch that applies relatively heavy preprocessing to the raw EMG signal. In parallel, there is less heavy preprocessing of the EMG signal to produce a processed EMG signal. This branch is described below.

In step 280, the EMG signal is processed to produce a processed EMG signal, such as an RMS of the EMG signal or a mean absolute value of the EMG signal. The RMS of the EMG signal may be computed as follows:

$$x_{rms}(t) = \sqrt{\frac{1}{T_2 - T_1} \int_{T_1}^{T_2} [x(t)]^2 dt}$$

where: $x_{rms}(t)$ is the RMS EMG signal; and $T_1$ and $T_2$ are the beginning and end of the time period covering the signal of interest, respectively.

In step 300, the inhalations of the user are detected based on the surrogate respiration signal produced by the processing steps 200.

The inhalations may be detected using the signal emg_hpf 550 using a simple threshold 555. If the signal rises above the threshold, an inhalation is detected. The threshold may, for example, be set at 0; however, the threshold may also be set at any other desired level. The threshold may also be derived in an adaptive data-dependent manner, meaning the position of the threshold may be determined based on, for example, the amplitude of the signal. This can be compared to the signal nasal_cannula 560, wherein the valleys of the signal represent inhalations and the peaks represent exhalations of the user, measured by way of a nasal cannula.

Looking to the twenty second period between 320 and 340*s*, it can be clearly seen that the emg_hpf signal detects multiple inhalations of the user; whereas, the nasal_cannula signal detects far fewer inhalations, with a period of roughly 10 seconds where no inhalations are detected at all. This discrepancy may occur due to the patient breathing through their mouth, rather than their nose, meaning that the inhalations are not detected by the nasal cannula. As the EMG signal is not dependent on whether the patient breathes through their mouth or nose, no inhalations are missed. This leads to a greater accuracy in overall inhalation detection and so in the computation of a neural respiratory drive measure.

In step 400, the neural respiratory drive measure is determined based on the detected inhalations and the processed EMG signal.

The neural respiratory drive of the user may be computed based on the neural respiratory drive measure. As the accuracy of the detected inhalations is improved, as described above, the accuracy of the neural respiratory drive is also improved.

Figure 3:
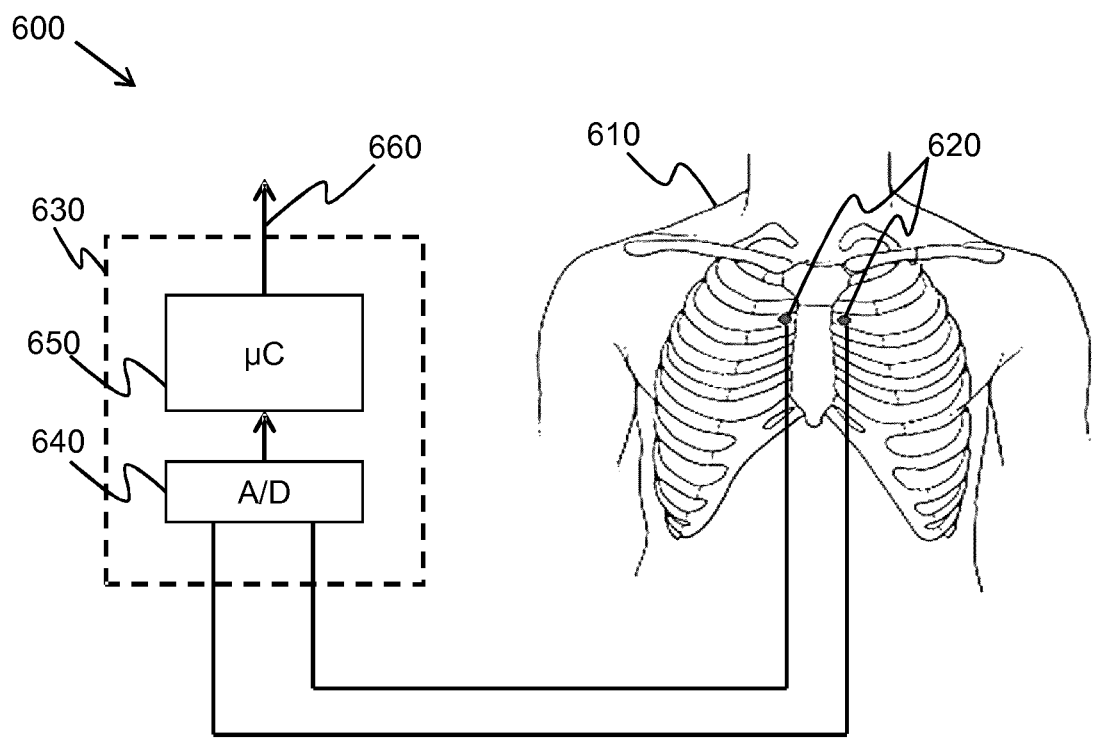
FIG. 3 shows an inhalation detection system.

FIG. 3 shows a system 600 for detecting inhalations of a user 610.

Two EMG electrodes 620 are provided at the second intercostal space of the user, with one electrode located at either side of the sternum. Alternatively, the electrodes may be located at the upper abdomen of the user, thereby measuring EMG signals from the diaphragm. The electrodes may be provided in a single patch to be administered to the user, or individually.

The EMG electrodes detect an EMG signal of the user, which may then be provided to a signal processing unit 630. The signal processing unit may contain an analogue to digital converter 640, which is adapted to convert the analogue EMG signal to a digital form. In this way, the EMG signal may be processed by a digital system.

The digitized EMG signal may then be provided to a controller 650 adapted to process the EMG signal to generate a surrogate respiration signal. The controller may also be adapted to detect inhalations of the user based on the surrogate respiration signal. In addition, the controller may also be adapted to process the EMG signal to produce a processed EMG signal and, based on the detected inhalations and processed EMG signal, determine neural respiratory drive measure of the user. The detected inhalations, or neural respiratory drive measure, may form the output 660 of the controller, which may then be used by a further processor to compute an NRD of the user. Alternatively, the computation of the NRD may be performed by the controller 650, in which case the output 660 may be the NRD of the user. The output of the controller may be provided to a user interface of the system, or it may be provided to further processing systems. The controller may be a microcontroller or any other suitable processor.

The sequence of processing steps given above is purely by way of example.

For example, any high pass filter operation may be implemented by a band pass filter, in that there will be a highest frequency region which is not of interest and can thus also be filtered out. Similarly, any low pass filter operation may be implemented by a band pass filter, in that there will be a lowest frequency region which is not of interest and can thus also be filtered out.

The different signal processing steps are explained above to make the operation of the method and system clear. In practice, the raw EMG signal will first be digitized and then all subsequent signal processing is implemented by a digital signal processing system. In such signal processing, the different processing steps are not necessarily individually distinguishable. Furthermore, some of the signal processing functions are optional.

For example, the downsampling step 240 is not fundamental to the underlying signal processing concept and is entirely optional.

The baseline removal, performed by the second high pass filter 270, is also optional, in that the previous envelope signal may be analyzed based on rising and falling edges, rather than applying a threshold to the baseline-removed version of the signal. In this case, the surrogate respiration signal would take the form of the emg_lpf plot 540 of FIG. 2, rather than the emg_hpf plot 550.

The initial spike removal may also not be used, since subsequent filtering operations may be sufficient to prevent corruption of the signal processing results.

Thus, in general terms, the signal processing comprises filtering to remove ECG contamination, determination of a signal absolute value or energy-like measure, followed by smoothing, and the inhalation phases can then be determined from the smoothed signal. The detected inhalation phases, and a processed EMG signal, can then be used to determine a neural respiratory drive measure of the user.

The invention enables a simple and easy to use, accurate and reproducible (automated) NRD measurement, which can be applied in the home to monitor the respiratory condition of a COPD patient, for example. The system is easy to use for the patient, since it is likely that the measurement will be self-administered and affordable. In particular, a single sensor patch may be used for both EMG signal collection and inhalation detection, without the need for a differential pressure sensor.

The system may be used to measure NRD, or any other respiratory effort parameter which takes account of the inspiratory and expiratory time intervals. As discussed above, embodiments make use of a signal processing unit. The signal processing unit can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for extracting a neural respiratory drive measure of a user, the method comprising:
   non-invasively obtaining a first EMG signal from a plurality of electrodes, at least two of the plurality of electrodes being disposed contralaterally;
   processing the first EMG signal with a first processing sequence to produce a processed EMG signal;
   processing the first EMG signal with a second processing sequence to produce a surrogate respiration signal, the second processing sequence and the first processing sequence being parallel to and independent from one another, wherein the surrogate respiration signal is obtained only from the first EMG signal;
   detecting inhalations of the user based on the surrogate respiration signal;
   time aligning the detected inhalations with the processed EMG signal; and
   determining the neural respiratory drive measure based on the time aligned detected inhalations and processed EMG signal.

2. A method as claimed in claim 1, wherein the processing of the first EMG signal to produce a surrogate respiration signal comprises performing spike removal on the first EMG signal.

3. A method as claimed in claim 1, wherein the processing of the first EMG signal to produce a surrogate respiration signal comprises applying a first high pass filter to the first EMG signal.

4. A method as claimed in claim 3, wherein the first high pass filter has a cutoff frequency of greater than or equal to 150 Hz.

5. A method as claimed in claim 3, wherein the processing of the first EMG signal to produce a surrogate respiration signal comprises applying a second high pass filter to the first EMG signal.

6. A method as claimed in claim 1, wherein the processing of the first EMG signal to produce a surrogate respiration signal comprises performing envelope detection on the first EMG signal, wherein the envelope detection comprises:
   applying a rectification operator to the first EMG signal, to generate a second EMG signal; and
   applying a low pass filter to the second EMG signal.

7. A method as claimed in claim 6, wherein the second EMG signal comprises an energy-like measure of the first EMG signal.

8. A method as claimed in claim 7, wherein the energy-like measure of the first EMG signal comprises at least one of a Teager-Kaiser energy and a conventional energy.

9. A method as claimed in claim 6, wherein the rectification operator comprises at least one of an absolute operator and a square operator.

10. A method as claimed in claim 1, wherein the processing of the first EMG signal to produce a surrogate respiration signal comprises downsampling the first EMG signal.

11. A method as claimed in claim 1, wherein the processing of the first EMG signal to produce a surrogate respiration signal comprises applying a median filter to the first EMG signal.

12. A method as claimed in claim 1, wherein the method further comprises computing the neural respiratory drive of the user based on the neural respiratory drive measure.

13. A computer program product, comprising a non-transitory computer usable medium having a computer readable program code embodied therein, the computer readable program code being adapted and configured to be executed to implement the method of claim 1.

14. A controller for determining a neural respiratory drive measure of a user in an EMG measurement system, wherein the controller is adapted to:
   non-invasively obtain a first EMG signal from a plurality of electrodes, at least two of the plurality of electrodes being disposed contralaterally;
   process the first EMG signal with a first processing sequence to produce a processed EMG signal;
   process the first EMG signal with a second processing sequence to produce a surrogate respiration signal, the second processing sequence and the first processing sequence being parallel to and independent from one another;

detect inhalations of the user based on the surrogate respiration signal;

time align the detected inhalations with the processed EMG signal; and determine the neural respiratory drive measure based on the time aligned detected inhalations and processed EMG signal, wherein the surrogate respiration signal is produced only from the first EMG signal.

15. An inhalation detection system comprising:

the plurality of EMG electrodes adapted to measure the first EMG signal; and a controller as claimed in claim 14.

* * * * *